US011033291B2

(12) United States Patent
Bright

(10) Patent No.: US 11,033,291 B2
(45) Date of Patent: Jun. 15, 2021

(54) SURGICAL DEVICE FOR USE IN ENDOSCOPIC CARPAL TUNNEL RELEASE (ECTR), ENDOSCOPIC CUBITAL TUNNEL RELEASE (ECUTR), AND ENDOSCOPIC PLANTAR FASCIITIS RELEASE (EPFR)

(71) Applicant: Nanice Medical Solutions, LLC, Trappe, PA (US)

(72) Inventor: Paul J. Bright, Ventnor, NJ (US)

(73) Assignee: NANICE MEDICAL SOLUTIONS LLC, Trappe, PA (US)

( * ) Notice: Subject to any disclaimer, the term of this patent is extended or adjusted under 35 U.S.C. 154(b) by 347 days.

(21) Appl. No.: 15/282,839

(22) Filed: Sep. 30, 2016

(65) Prior Publication Data

US 2017/0095266 A1    Apr. 6, 2017

Related U.S. Application Data

(60) Provisional application No. 62/236,728, filed on Oct. 2, 2015.

(51) Int. Cl.
*A61B 17/32* (2006.01)
*A61B 17/00* (2006.01)

(52) U.S. Cl.
CPC ............. *A61B 17/320036* (2013.01); *A61B 2017/0023* (2013.01); *A61B 2017/320052* (2013.01)

(58) Field of Classification Search
CPC .... A61B 17/320036; A61B 17/320016; A61B 17/32002; A61B 2017/32004; A61B 2017/320044; A61B 2017/320052; A61B 2017/320056; A61B 2017/32006; A61B 2017/320072–320075; A61B 2017/320077–320078; A61B 17/00234; A61B 1/00071; A61B 1/00087; A61B 1/00101; A61B 1/01; A61B 1/012; (Continued)

(56) References Cited

U.S. PATENT DOCUMENTS 5,507,800 A    4/1996   Strickland
5,827,311 A   10/1998   Berelsman et al.
(Continued)

FOREIGN PATENT DOCUMENTS

WO    2015171785 A1    11/2015

OTHER PUBLICATIONS

Arthrex Inc., Centerline Endoscopic Carpal Tunnel Release Surgical Technique, Centerline Carpal Tunnel Release, Entire Document, Brochure No. LT1-0412-EN_C, United States.
(Continued)

*Primary Examiner* — Ryan N Henderson
*Assistant Examiner* — Pamela F Wu
(74) *Attorney, Agent, or Firm* — Schott, P.C.

(57) ABSTRACT

A disposable, sterile guide constructed of medically-acceptable plastic used for compartmentalizing and therefore protecting the ligament or fascia during three different orthopedic surgical procedures: ECTR, ECuTR, and EPFR. This device reduces the risk of damage to any other part of the surrounding anatomy. The device is disposable and packaged so as to be sterile and therefore readily usable by the surgeon means that it can reduce the risk of infection and is a less expensive alternative to traditional non-disposable, metal instruments that must be sterilized prior to each procedure.

12 Claims, 8 Drawing Sheets

(58) Field of Classification Search
CPC . A61B 1/018; A61B 17/3421; A61B 17/3423;
A61B 2017/3425; A61B 2017/3445;
A61B 2017/3449; A61B 17/3462; A61B
17/3415; A61B 2017/3433; A61B
2017/3429; A61B 2017/320082; A61B
2017/320093; A61B 17/3205; A61B
17/3209; A61B 17/32093; A61B 17/34;
A61B 17/3401; A61B 17/3403; A61B
2017/3405; A61B 2017/3407; A61B
17/22072; A61B 17/22074–22075; A61B
17/22077–22078; A61B 1/00064; A61B
1/0008; A61B 1/00089; A61B 1/00096
USPC ....... 600/183, 184, 190, 197, 204, 201, 203,
600/227, 231
See application file for complete search history.

(56) References Cited

U.S. PATENT DOCUMENTS

| | | | |
|---|---|---|---|
| 5,908,431 | A | 6/1999 | Battenfield |
| 6,283,948 | B1 | 9/2001 | McKernan et al. |
| 8,252,011 | B1 * | 8/2012 | Forrester ........ A61B 17/320016 |
| | | | 606/167 |
| 8,523,892 | B2 | 9/2013 | Rehnke et al. |
| 8,672,960 | B2 * | 3/2014 | Briganti ......... A61B 17/320036 |
| | | | 606/170 |
| 8,852,191 | B2 | 10/2014 | Bertram |
| 8,882,772 | B2 | 11/2014 | Solsberg et al. |
| 8,951,273 | B1 | 2/2015 | Fard |
| 2005/0159730 | A1 * | 7/2005 | Kathrani ............ A61B 17/3421 |
| | | | 604/541 |
| 2008/0200758 | A1 * | 8/2008 | Orbay ................ A61B 1/00048 |
| | | | 600/112 |
| 2010/0280368 | A1 | 11/2010 | Can et al. |
| 2014/0066709 | A1 * | 3/2014 | Mirza .............. A61B 17/32002 |
| | | | 600/106 |
| 2014/0121456 | A1 | 5/2014 | McCormack et al. |
| 2014/0371526 | A1 | 12/2014 | Mirza et al. |
| 2015/0272617 | A1 * | 10/2015 | MacDonald ............. A61B 1/05 |
| | | | 600/110 |
| 2016/0157881 | A1 | 6/2016 | Seymour et al. |
| 2016/0192828 | A1 * | 7/2016 | Sexton ............... A61B 17/3421 |
| | | | 600/114 |
| 2016/0287322 | A1 * | 10/2016 | Solsberg ............ A61B 17/3417 |
| 2016/0345998 | A1 * | 12/2016 | Seymour ........ A61B 17/320016 |

OTHER PUBLICATIONS

Microaire Surgical Instruments, SmartRelease ECTR Endoscopic Carpal Tunnel Release Surgical Technique, Entire Document, Charlottesville, VA, United States.
Smith&Nephew, Ectra II Carpal Ligament System, Entire URL, United States.
Einhorn, N., and Leddy, J.P., "Pitfalls of Endoscopic Carpal Tunnel Release," Orthopedic Clinic of North America, vol. 27, No. 2, pp. 373-380 (1996).
Non Final Office Action received for U.S. Appl. No. 16/001,887, dated Aug. 22, 2019, 13 pages.
Final Office Action received for U.S. Appl. No. 16/001,887, dated Jan. 8, 2020, 19 pages.
Notice of Allowance received for U.S. Appl. No. 16/001,887, dated Jun. 18, 2020, 9 pages.

* cited by examiner

SURGICAL DEVICE FOR USE IN ENDOSCOPIC CARPAL TUNNEL RELEASE (ECTR), ENDOSCOPIC CUBITAL TUNNEL RELEASE (ECUTR), AND ENDOSCOPIC PLANTAR FASCIITIS RELEASE (EPFR)

BACKGROUND

Endoscopic Carpal Tunnel Release (ECTR), Endoscopic Cupital Tunnel Release (ECuTR), and Endoscopic Plantar Fasciitis Release (EPFR) are three surgical procedures used to relieve symptoms in the hand, elbow, and heel, respectively. During each procedure, the surgeon makes a small incision and inserts a thin tube called an endoscope with a tiny camera attached to it to view the affected area. The surgeon then inserts a cutting instrument through this same, single portal to perform the procedure. The benefit of endoscopic procedures is that they require smaller incisions, leading to the diminution of early post-operative pain, decreasing the amount of recovery time, and expediting patients' return to regular activity. These smaller incisions, however, inherently mean that visualization of the affected area is more restricted as compared to procedures such as Open Carpal Tunnel Release (OCTR), during which one large incision is employed. Throughout the history of endoscopic procedures, surgeons have worked to improve methods of visualization in order to improve safety levels and outcomes.

Current guides for surgery are usually stainless steel and come in two pieces, which means there are sterility issues between surgeries and also the ever-present risk of the pieces becoming unattached in surgical contexts. This is especially true because current scope pieces engage one another in a friction attachment.

SUMMARY OF THE EMBODIMENTS

The device described herein is a disposable, sterile guide constructed of medically-acceptable plastic used for compartmentalizing and therefore protecting the ligament or fascia during three different orthopedic surgical procedures: ECTR, ECuTR, and EPFR. This device reduces the risk of damage to any other part of the surrounding anatomy. The fact that the device is disposable and packaged so as to be sterile and therefore readily usable by the surgeon means that it can reduce the risk of infection and is a less expensive alternative to traditional non-disposable, metal instruments that must be sterilized before each procedure.

DETAILED DESCRIPTION OF THE EMBODIMENTS

Figure 1:
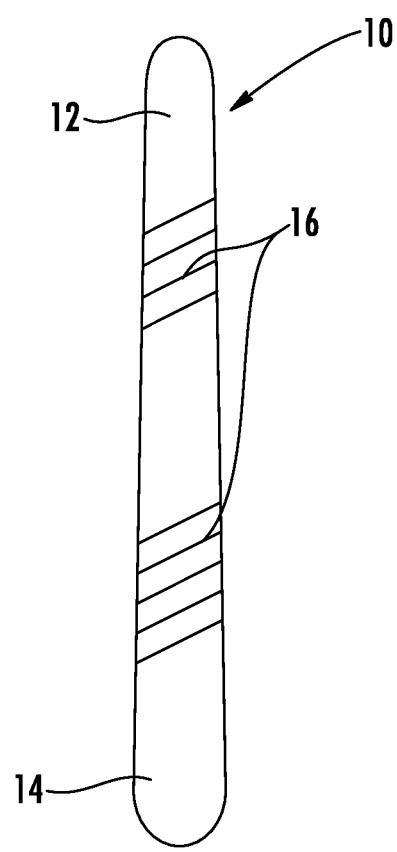
FIG. 1 shows a dilator used to prepare a surgical area for the device.

The following surgical description may be employed for using the surgical device shown the figures in at least three different surgeries: Endoscopic Carpal Tunnel Release (Hand), Endoscopic Cubital Tunnel Release (Elbow), and Endoscopic Plantar Fasciitis Release (Heel).

After making an incision, the surgeon may use a dilator 10 (FIG. 1) to dilate the surgical area. The dilator may be about 6 inches long and taper at a broader end 14 to a narrow end 12 from 6 mm to 4 mm. The dilator may include hand grips 16 marked to minimize slipping.

To make room for the guide device to fit atop and below the targeted ligament or fascia, the surgeon may insert the device 100, 300, 400 in order to compartmentalize the ligament or fascia. The surgeon may then use the endoscope that has been inserted through a cameral passage or hole to visualize the ligament or fascia area to ensure that there are no other parts of the anatomy, such as nerves or tendons, obstructing the incision path.

If the incision path is clear, the surgeon can either antegrade cut or retrograde cut the ligament or fascia in a safe environment by inserting the knife through the appropriate slot, because the device or guide has helped the surgeon to compartmentalize the ligament or fascia to be incised, isolating it from other parts of the anatomy that could otherwise be in jeopardy of being inadvertently cut.

The endoscopic camera and the knife may work independently of each other inside the guide, making it safer for the surgeon to look ahead of the knife when needed.

FIG. 1 is a drawing of the surgical device 100 for assistance in endoscopic surgical procedures, especially those discussed above but not necessarily limited thereto.

Figure 2A:
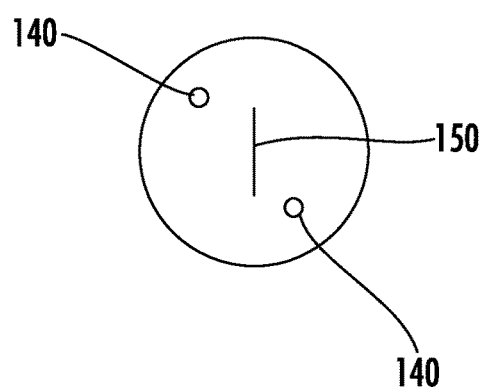
FIGS. 2A and 2B show side and elevation views of the device.
Figure 2B:
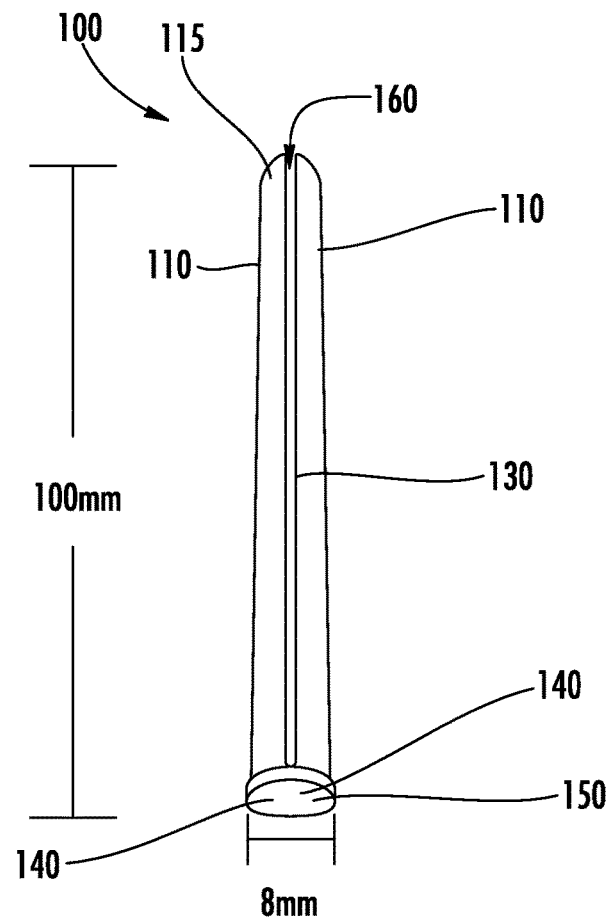

The surgical device 100 may be 100 mm in length, 8 mm wide, and constructed from ABS plastic. The device 100 may be hollow and cylindrical with 3 mm-thick plastic prongs 110 separated by a 2 mm gap 130. FIG. 2 shows one end of the device 100, which is closed with the exception of three holes: the upper and lower circular holes 140 may be each 2.5 mm in diameter, may be used for the endoscopic camera, and may be located on either side of the 5 mm long slot 150 used for the knife. The location of the upper and lower circular holes 140 on either side of the slot 150 gives the surgeon the ability to use the endoscopic camera to visualize the surgical field more comprehensively from many angles before a cut is made to avoid damaging other portions of the anatomy.

Figure 6A:
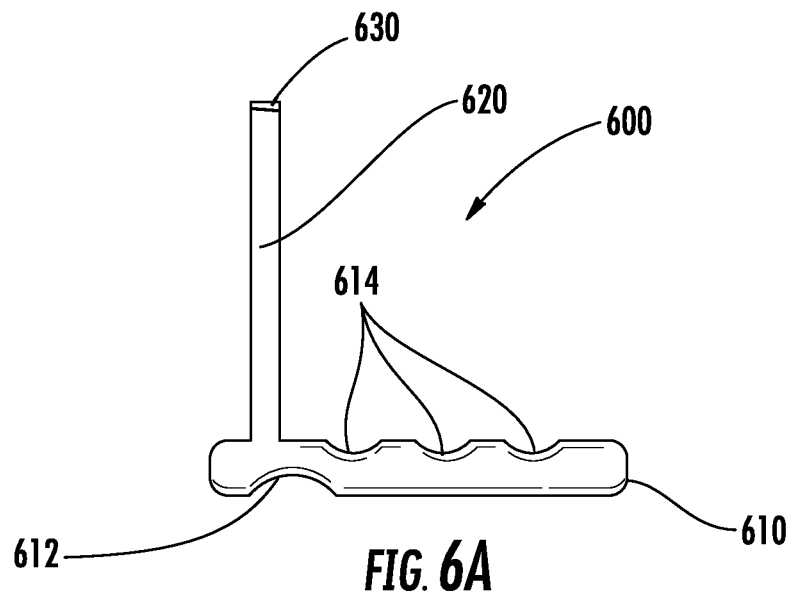
FIGS. 6A and 6B show blade and tool variants used with the device.
Figure 6B:
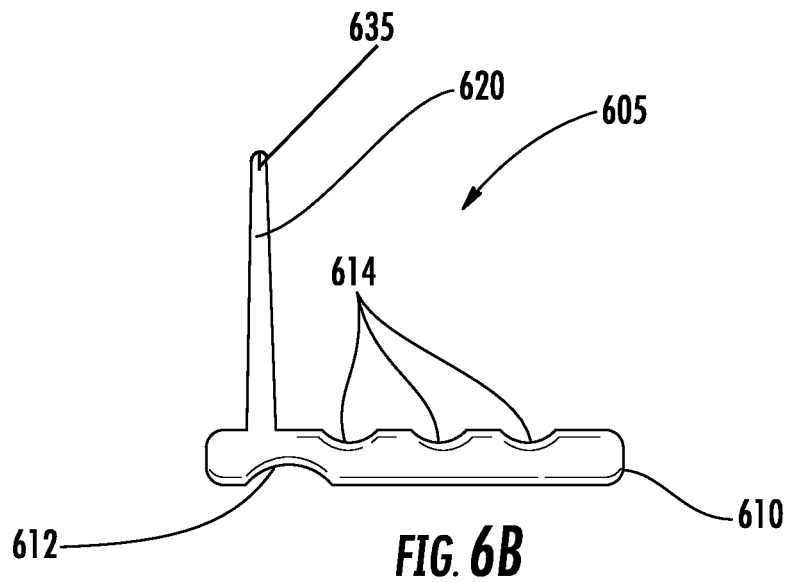

FIGS. 6A and 6B show tools like the knife (600) and wire 605 for use with the device 100, 300, or 400. In use, a surgeon may grasp the knife 600 or wire 605 by a handle 610 that may include finger cutouts for a thumb 612 and fingers 614. The tool 600, 605 may comprise both a handle portion 610 and working portion 620. On the knife 600, the working portion 620 is sized to fit within the slot 150, 380 and includes a blade 630 for performing the incisions as the blade moves within the slot 150, 380.

The wire tool 605 operates similarly to the knife tool 600 except that its working end 620 includes a narrow wire end 635 for removing fine tissue or moving a nerve out of the way of a later incision by the knife tool 600. The wire end 635 may extend in any direction (upwards towards the viewer as shown in FIG. 6B being on alternative) but importantly fits within the knife slot.

The guide device 100 may include a wedge-shaped protrusion 160 at a terminal end of one (or both) of the prongs 110 that may help in clearing tissue from within the gap 130. The wedge may be sharp, extend only from the narrow terminal end 115 of the prongs 110 or extend across the width of the prong 110.

Figure 3A:
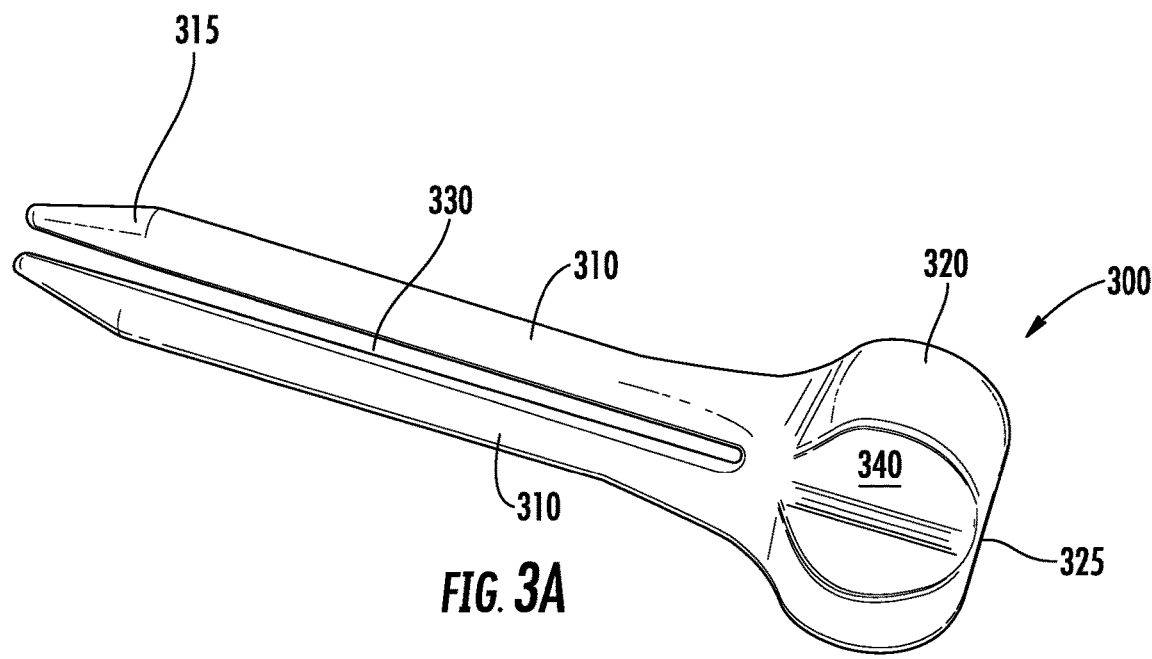
FIGS. 3A-3D show an alternate embodiment of the device.
Figure 3B:
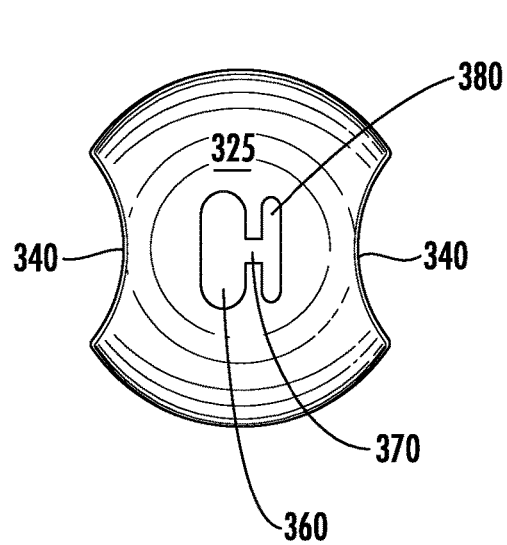
Figure 3C:
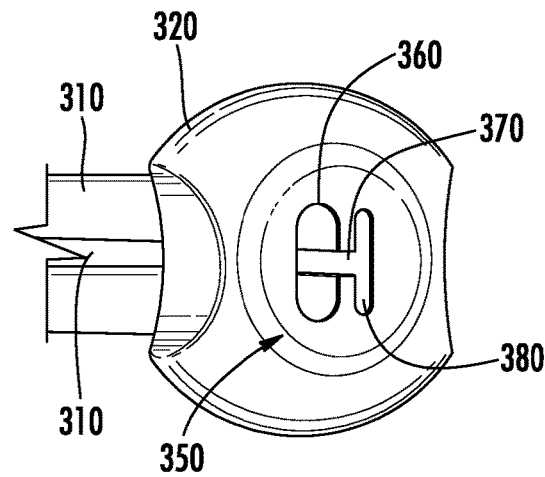
Figure 3D:
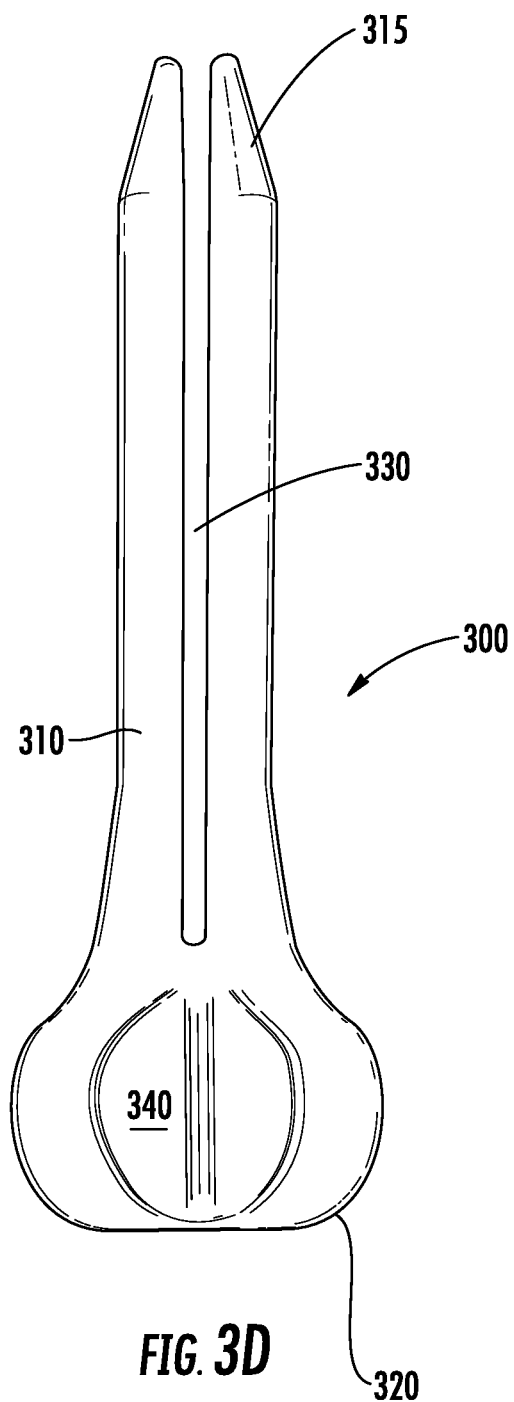

FIGS. 3A-3E show an alternate embodiment of the device from FIG. 2. As can be seen in FIG. 3A, the device 300 includes prongs 310 separated by a gap 330 similar to the geometry of FIGS. 1 and 2. The device 300's prongs 310 have a narrow terminal end 315 opposite a head portion 320 having finger cutouts 340 that in combination help in grasping the device 300. This head portion 320 helps in device 300 insertion into the patient as well as removal, and also positioning the device 300 during surgery.

The head portion end face 325 has a tool opening 350 therein. The tool opening 350 passes through the head portion 320 and is in fluid communication with the gap 330. The tool opening may include a camera opening 360 and a blade slot 380 separated by an open space 370 that allows for a small tool insertion to remove unwanted tissue or other waste from the scope or camera opening.

The camera opening is for scope insertion, and allows the surgeon to inspect the incision, ensure the area to be incised is clear of nerves, and generally allow the surgeon to see the work to be performed. As can be best seen in FIG. 4B, the camera may travel within one of the prongs 310 within a camera groove 312 formed along and within each prong 310. A second groove 314 may also include room for the tools 600, 605.

Figure 4A:
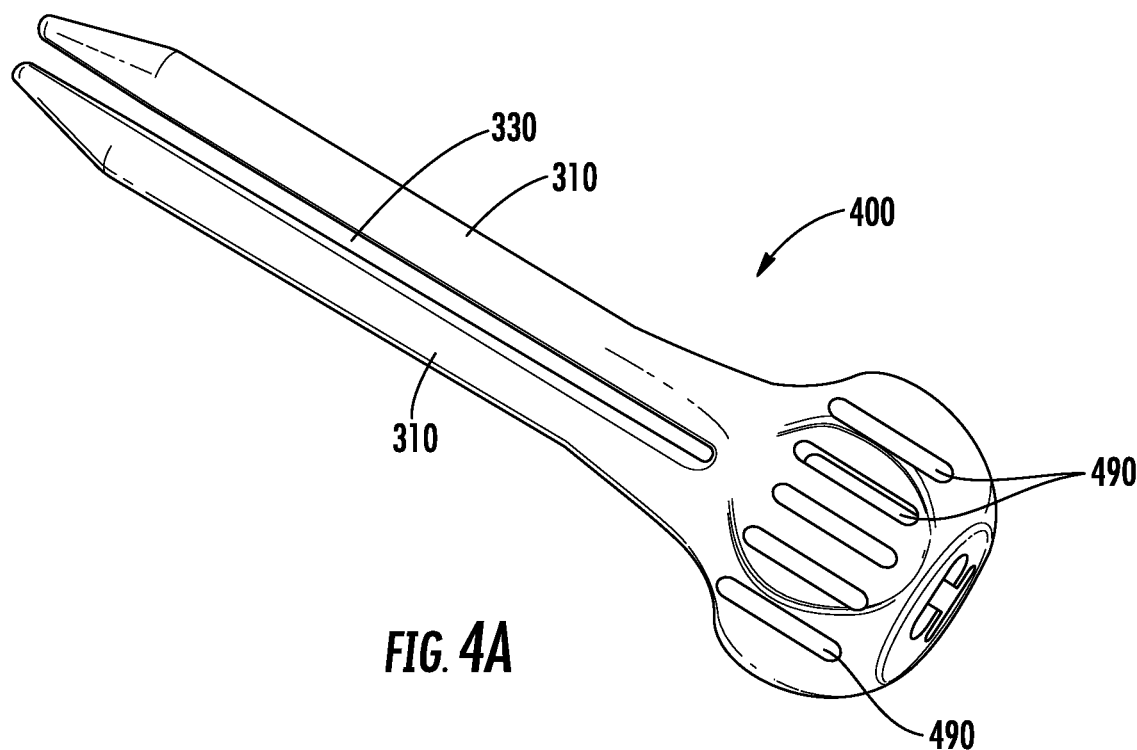
FIGS. 4A-4C show a further alternate embodiment of the device.
Figure 4B:
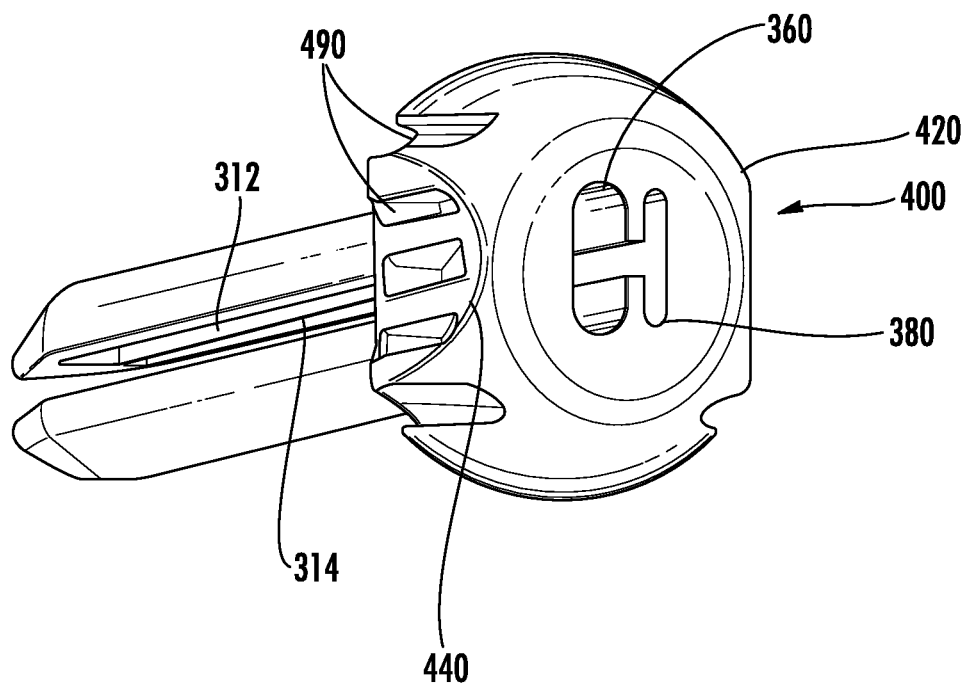
Figure 4C:
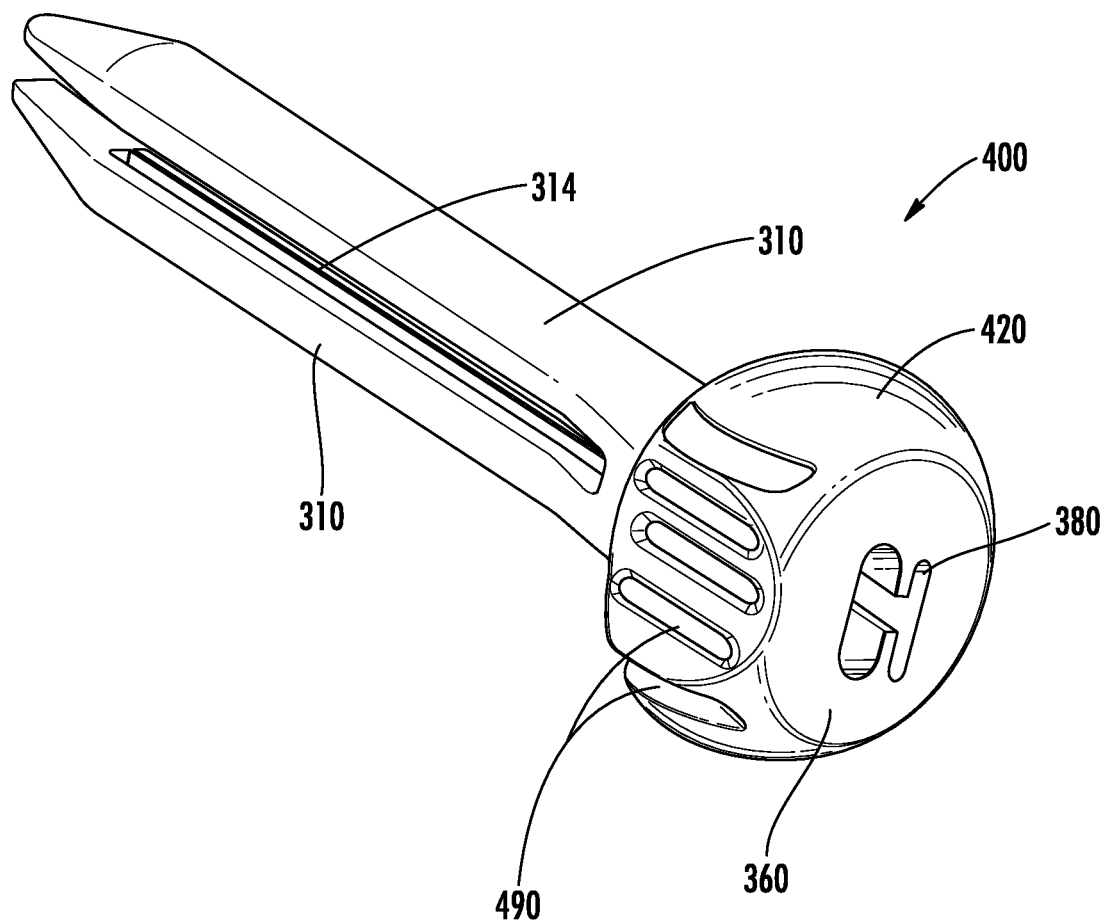

The guide device 400 in FIGS. 4A-C is similar to the one in FIGS. 3A-3D except for finger grooves 490. These finger grooves 490 extend into the head portion 420 and serve two purposes: First, they act to help a surgeon grasp the guide 400 during insertion, when slipping tools can be a problem. Second the finger grooves 490 help with cooling the device 400 during manufacture, allowing for uniform cooling and thus, decrease defect formation.

Figure 5:
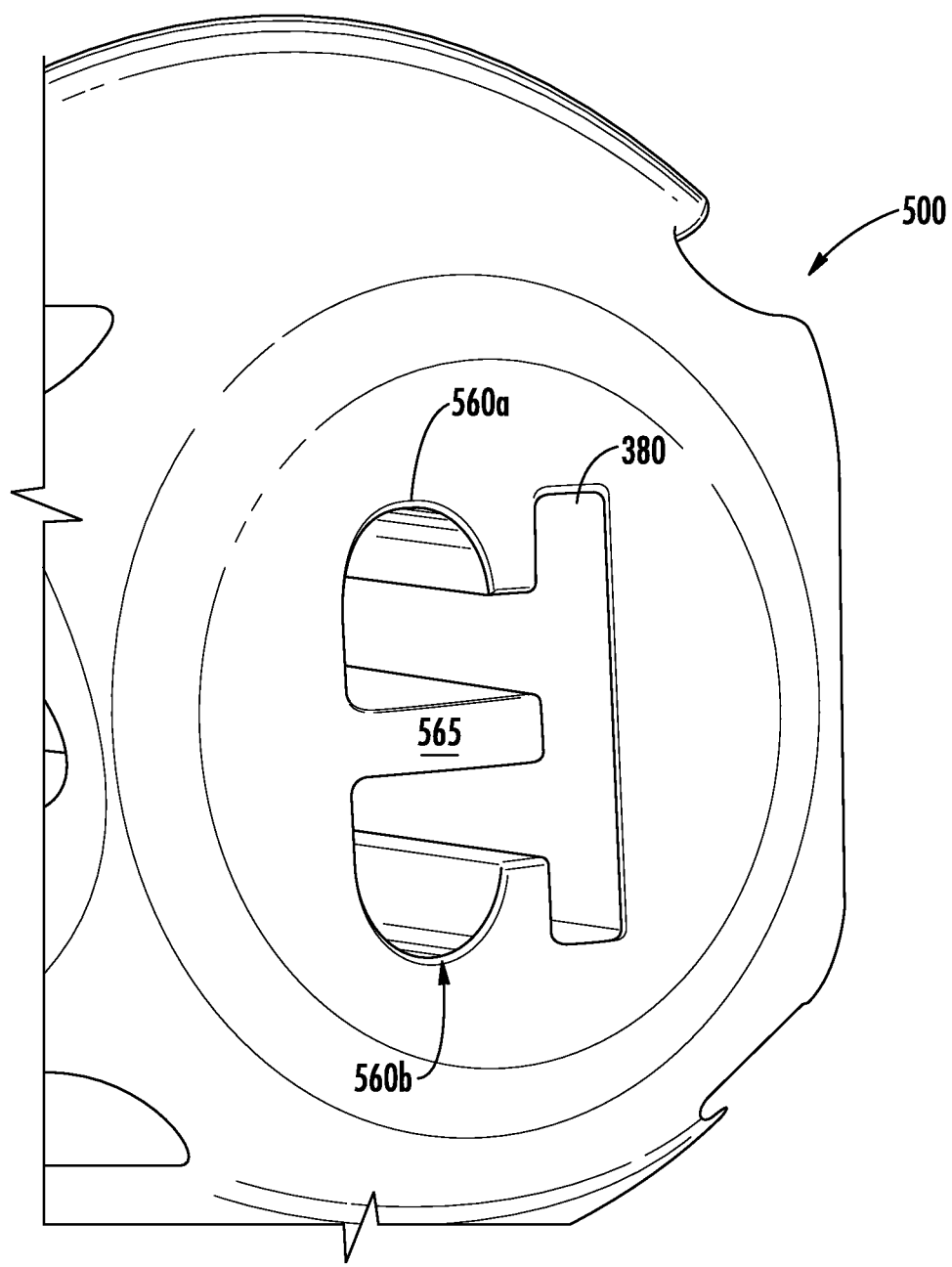
FIG. 5 shows another alternate embodiment of the device.

FIG. 5 shows a further alternate design of the device 500. Within this device, a shelf 565 extends to divide the camera opening halves 560a, and 560b. This helps support the scope when inserted into the camera openings.

The device guide described herein may be shipped in sterile packaging to ensure sterility in use, which overcomes the issues with certain steel guides that must be sterilized on each use. Because it is plastic, the device may be discarded after use and easily replaced, thus making it less expensive than a stainless steel tool but also safer.

In use, the device may encompass the transverse ligament therefore avoiding the challenge of synovium and fat dropping into view when cutting the ligament. This improves visibility because the surgeon isn't cutting underneath the ligament but encapsulating the ligament and cutting either antegrade or retrograde and seeing the ligament with a top view as well as bottom view while cutting.

Further, the top and bottom portions of the guide encompasses the ligament and that makes the guide safer for ECTR.

As shown herein, the guide is as a unitary construction molded in plastic, although it is possible to 3D print the guide as well. Multi-piece construction is possible and may be advantageous in certain contexts.

The device is also made to accommodate both left and right hand for same procedure by just turning it upside down to always cut on the ulnar safe side of the hand, which is the ulnar side of anatomy.

While the invention has been described with reference to the embodiments above, a person of ordinary skill in the art would understand that various changes or modifications may be made thereto without departing from the scope of the claims.

The invention claimed is:

1. A surgical guide comprising:
a unitary head comprising a tool opening therethrough; and
two prongs unitarily molded directly with the unitary head, wherein the prongs are of equal length and width, wherein a gap separates the prongs, wherein a gap distance between the prongs is substantially maintained in use;
wherein the gap separating the prongs is in fluid communication with the tool opening in the head;
wherein the tool opening in the head comprises a blade slot configured to receive a cutting tool and two camera openings, either one of the camera openings configured to receive a camera.

2. The surgical guide of claim 1, wherein the head includes finger cutouts to assist in holding the guide.

3. The surgical guide of claim 1, wherein at least one of the two prongs have a terminal end that is narrower than a prong end near the head.

4. The surgical guide of claim 1, wherein one of the prongs comprises a wedge extending therefrom towards the opposite prong and into the gap.

5. The surgical guide of claim 1, wherein the guide is made from ABS plastic.

6. The surgical guide of claim 1, further comprising a tool including a working portion sized to fit within the blade slot.

7. The surgical guide of claim 6, wherein the tool further comprises a handle portion having finger cutouts.

8. The surgical guide of claim 6, wherein the tool comprises a blade.

9. The surgical guide of claim 6, wherein the tool comprises a wire end.

10. The surgical guide of claim 6, further comprising a scope for insertion into one of the camera openings.

11. The surgical guide of claim 1, wherein the gap distance is 2 mm.

12. The surgical guide of claim 11, wherein the two prongs are the only prongs.

* * * * *